(12) United States Patent
Diamond et al.

(10) Patent No.: US 8,516,641 B2
(45) Date of Patent: Aug. 27, 2013

(54) TOOTHBRUSH

(75) Inventors: Jean Diamond, Carpenterstown (IE);
David Diamond, Carpenterstown (IE)

(73) Assignee: Jean Diamond, Dublin (IE)

( * ) Notice: Subject to any disclaimer, the term of this patent is extended or adjusted under 35 U.S.C. 154(b) by 848 days.

(21) Appl. No.: 12/594,858

(22) PCT Filed: Apr. 10, 2008

(86) PCT No.: PCT/EP2008/002824
§ 371 (c)(1),
(2), (4) Date: Oct. 12, 2009

(87) PCT Pub. No.: WO2008/125269
PCT Pub. Date: Oct. 23, 2008

(65) Prior Publication Data
US 2010/0132140 A1    Jun. 3, 2010

(30) Foreign Application Priority Data

Apr. 11, 2007    (IE) .................................. S2007/0256

(51) Int. Cl.
*A61C 17/26* (2006.01)
(52) U.S. Cl.
USPC .............................................. 15/22.1; 15/23
(58) Field of Classification Search
USPC ............... 15/22.1, 22.2, 22.4, 23, 28
See application file for complete search history.

(56) References Cited

U.S. PATENT DOCUMENTS

| | | | | |
|---|---|---|---|---|
| 1,927,566 A * | 9/1933 | Hawk | ................ | 15/23 |
| 3,168,834 A * | 2/1965 | Smithson | ................ | 74/23 |
| 3,379,906 A * | 4/1968 | Spohr | ................ | 310/50 |
| 3,489,936 A * | 1/1970 | Boyles | ................ | 310/47 |
| 3,524,088 A * | 8/1970 | Ryckman, Jr. | ................ | 310/50 |
| 3,546,501 A * | 12/1970 | Kircher | ................ | 310/50 |
| 3,562,566 A * | 2/1971 | Kircher | ................ | 310/80 |
| 3,588,936 A * | 6/1971 | Duve | ................ | 15/22.1 |
| 3,661,018 A * | 5/1972 | Keefer et al. | ................ | 74/22 R |
| 4,397,055 A * | 8/1983 | Cuchiara | ................ | 15/22.1 |
| 4,710,995 A * | 12/1987 | Joyashiki et al. | ................ | 15/22.1 |
| 4,756,202 A * | 7/1988 | Kawamoto | ................ | 74/23 |
| 4,791,945 A * | 12/1988 | Moriyama | ................ | 15/22.1 |
| 5,442,827 A * | 8/1995 | Hommann | ................ | 15/22.1 |
| 7,156,108 B2 * | 1/2007 | Xin | ................ | 132/322 |
| 2006/0117506 A1 | 6/2006 | Gavney, Jr. et al. | | |
| 2007/0006403 A1 | 1/2007 | DePuydt et al. | | |

FOREIGN PATENT DOCUMENTS

| | | | |
|---|---|---|---|
| DE | 8713194 | | 11/1987 |
| EP | 0968686 | | 1/2000 |
| JP | 5-137616 | * | 6/1993 |
| JP | 5-199918 | * | 8/1993 |
| JP | 5-207913 | * | 8/1993 |
| JP | 7-213342 | * | 8/1995 |
| JP | 9-24058 | * | 1/1997 |

* cited by examiner

*Primary Examiner* — Mark Spisich
(74) *Attorney, Agent, or Firm* — Porter Wright Morris & Arthur, LLP (57) ABSTRACT

The present invention provides a toothbrush (710), in particular a mechanical toothbrush (710) more commonly known as an electric toothbrush (710), which includes a spherical brush head (712) which is capable of undergoing at least first (720) and second (722) independent brushing motions in order to improve the overall brushing effectiveness.

23 Claims, 8 Drawing Sheets

TOOTHBRUSH

FIELD OF THE INVENTION

This invention relates to a toothbrush, and in particular a toothbrush having a spherical head and which is adapted to impart a wide range of different movements to the head in order to give the user the facility to choose the preferred and most suitable direction of brushing action for each part of the mouth and tongue.

BACKGROUND OF THE INVENTION

Toothbrushes, and in particular mechanised or electric toothbrushes, are well known and are available with a number of different modes of operation.

Mechanised toothbrushes having brush heads capable of rotational, oscillatory and pulsating motion are known in the art. The motion of the brush head is driven mechanically so that the user need only position the toothbrush at a particular location in the mouth. The brushing action is provided by a mechanical drive in order to brush teeth, tongue, gums and any other parts of the mouth. This reduces the manual force required to clean the teeth using the mechanical toothbrush compared to a manual toothbrush where the user provides the brushing motion and also provides brushing which could not conveniently be replicated manually.

Some current mechanised toothbrushes exhibit a brushing motion which brushes off the gum rather than laterally across the teeth or towards the gum. Brushing toward the gum can cause material to be forced underneath the leading edge of the gum or may strip the leading edge of the gum from the teeth. Current mechanised toothbrushes provide various means to brush of the gum in only certain parts of the mouth. These brushes are not capable of providing brushing off the gum action in parts of the mouth.

A method of effectively cleaning the surface of the tongue is to brush the tongue in a forward direction only.

In order to effectively clean the longitudinal indentations on the inner surfaces of the upper and lower front teeth it is necessary to exercise brushing motion parallel to their length and off the gum.

Known toothbrushes provide dual, multi directional or scatter brushing motion. The direction of the brushing motion produced by mechanised toothbrushes is generally the same irrespective of the part of the mouth or teeth with which they are in contact. However, this single non-variable motion is not effective or efficient in cleaning every the part of the teeth, gums and tongue.

It is one object of the present invention to provide a toothbrush which can implement the modified bass method for brushing teeth. The modified bass method is known and recommended by many dentists. This method involves making small circular motions with a toothbrush to clean plaque from the gum line and from the indented ridge in a tooth which runs along the gum line at the base of the tooth.

The bass modified method fails to provide fully effective brushing to parts of the teeth. For example, it does not reach certain areas between the teeth with sufficient effectiveness. However the modified bass method effectively addresses cleaning the indented ridge which is one of the most problematic areas of the teeth in terms of plaque accumulation and debris accumulation.

The modified bass method can be difficult to manually exercise and the toothbrush can mechanically simulate the brushing method. However it is a most effective and safe method of brushing teeth as the brush movements can be oriented in different directions to afford the most suitable brushing direction in each of the different parts of the mouth.

SUMMARY OF THE INVENTION

The present invention therefore provides a toothbrush comprising a brush head; and drive means adapted to impart at least first and second independent brushing motions to the head.

Preferably, the head is substantially spherical.

Preferably, the head comprises two substantially hemispherical sections.

Preferably, the head is rotatable about a first axis when undergoing the first brushing motion and independently about a second axis when undergoing the second brushing motion.

Preferably, the first and second axes are substantially perpendicular.

Preferably, the first and second axes pass through the centre of the head.

Preferably, the head is continuously rotatable in a given direction about the first and/or second axis.

Preferably, the head comprises an array of bristles extending outwardly therefrom.

Preferably, the bristles on the first and second hemispherical sections, at or adjacent the interface between the sections, are oriented to converge in order to create a protective covering substantially surrounding the interface.

Preferably, the drive means comprises at least one drive shaft arranged to impart one or both brushing motions to the head.

Preferably, the at least one drive shaft is arranged to reciprocate in order to impart the first brushing motion to the head, and to rotate substantially about a longitudinal axis of the drive shaft in order to impart the second brushing motion to the head.

Preferably, the drive means comprises means for translating the reciprocating motion of the at least one drive shaft into rotary motion of the head about a first axis.

Preferably, the translating means comprises a crankshaft.

Preferably, the translating means comprises at least one cam connected to the head and a corresponding follower connected to the drive shaft.

Preferably, the follower comprises a bushing surrounding the cam.

Preferably, the drive means comprises first and second drive shafts, the first shaft being arranged to impart the first brushing motion to the head and the second shaft being arranged to impart the second brushing motion to the head.

Preferably, the first and second drive shafts are concentric.

Preferably, the drive means comprises at least one motor arranged to drive the first and second shafts.

Preferably, the drive means comprises a clutch displaceable between an engaged and a disengaged state, in the engaged state enabling synchronous rotation of the first and second shafts, and in the disengaged state enabling independent rotation of the first shaft.

Preferably, the toothbrush comprises means for immobilising the second shaft, in a predetermined orientation, when the clutch is in the disengaged state.

Preferably, the drive means comprises a pair of bevel gears located within the head, a first gear fixed to the first shaft and a second gear meshing with the first gear and mounted on an axle to which the pair of hemispherical head sections are mounted.

Preferably, the second shaft is connected to a support which carries the axle.

Preferably, the second shaft is connected to a support on which the head is retained.

DETAILED DESCRIPTION OF THE DRAWINGS

Figure 1:
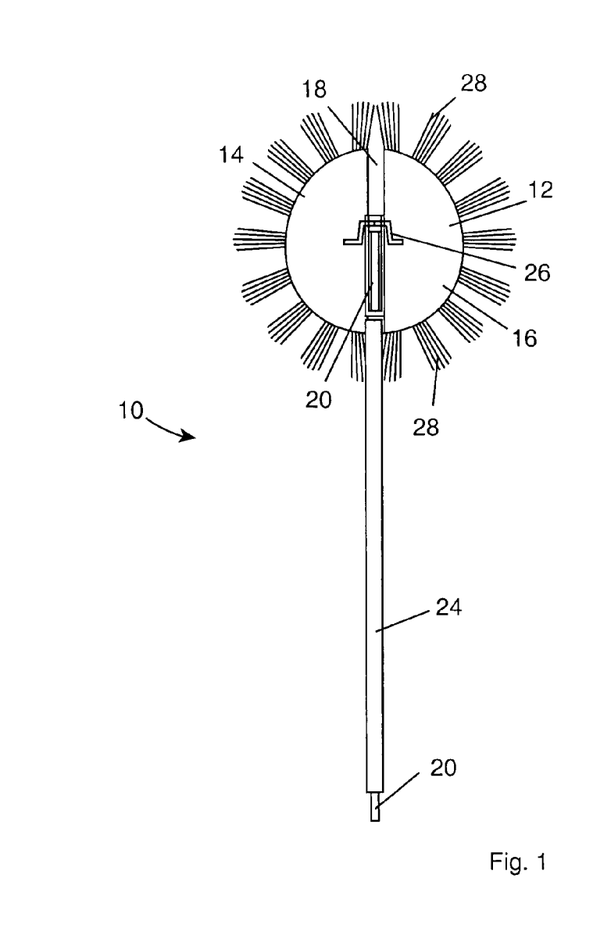
FIG. 1 is a cross sectional front view of a tooth brush head according to an aspect of a first embodiment of the present invention.
Figure 2:
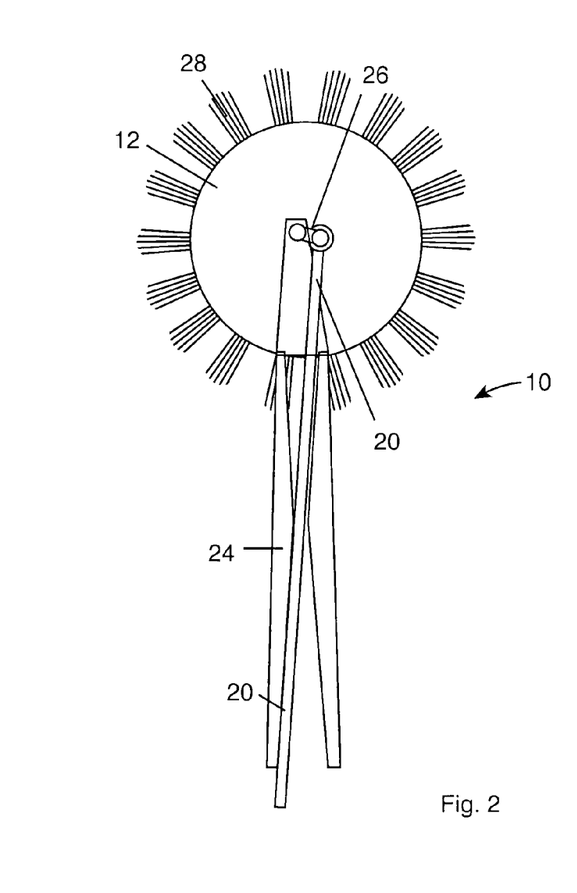
FIG. 2 is a cross sectional side view of the toothbrush head of FIG. 1.

Referring to FIGS. 1 and 2 of the accompanying drawings, there is illustrated part of a toothbrush 10 according to a first embodiment of the present invention. The toothbrush 10 has a brush head 12, which in the embodiment illustrated is comprised of a first hemispherical head section 14 and a second hemispherical head section 16. The hemispherical head sections 14, 16 are substantially hemispherical in shape and mounted closely to one another giving the brush head 12 an overall substantially spherical shape. The hemispherical head sections 14, 16 are each less than the full 180 degree hemispheres by a number of degrees to allow a channel 18 between the hemispherical head sections 14, 16 while maintaining the overall substantially spherical shape of the brush head 12. It will be appreciated that the hemispherical head sections 14, 16 can be any other shape, including semi ovoid, which affords the requisite properties.

The toothbrush 10 further comprise drive means in the form of a first or inner drive shaft 20 which is housed within a support sleeve 24 which in use will extend from or form part of a handle portion (not shown) of the toothbrush 10. The support sleeve 24 also ensures that the moving parts of the drive means, in particular the first drive shaft 20, are not contactable by a user of the toothbrush for safety reasons, and in addition provides a protective cover for the drive means in order to ensure the longevity of same. The drive shaft 20 extends up through the sleeve 24 and exits same to pass through the channel 18 where it terminates within the brush head 12. The drive shaft 20 is attached to the brush head 12 internally thereof to partially support its weight and, as described hereinafter, to impart at least first and second independent brushing motions to the head 12.

Figure 3:
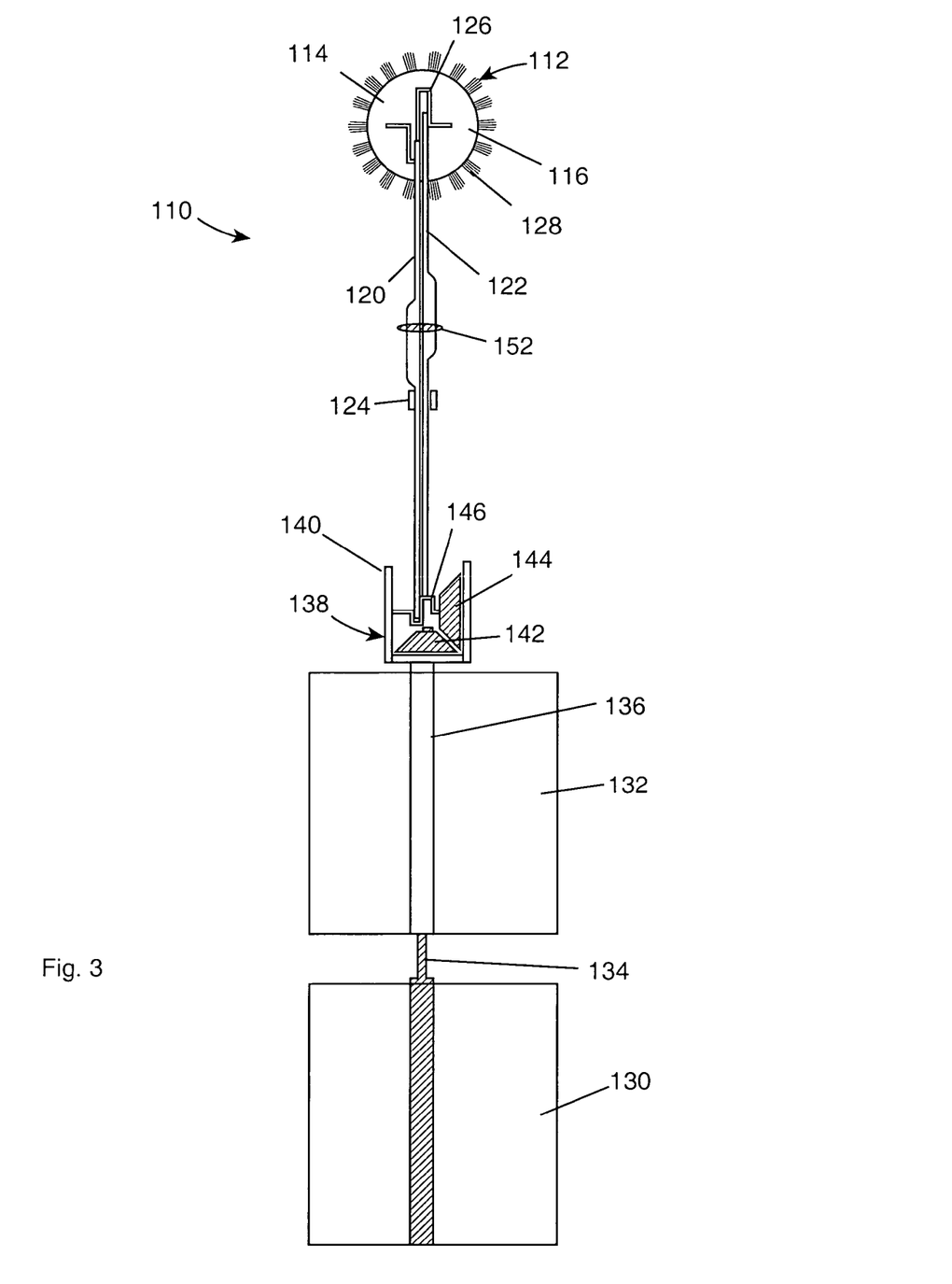
FIG. 3 is a cross sectional front view of a toothbrush according to an aspect of a second embodiment of the present invention.
Figure 12:
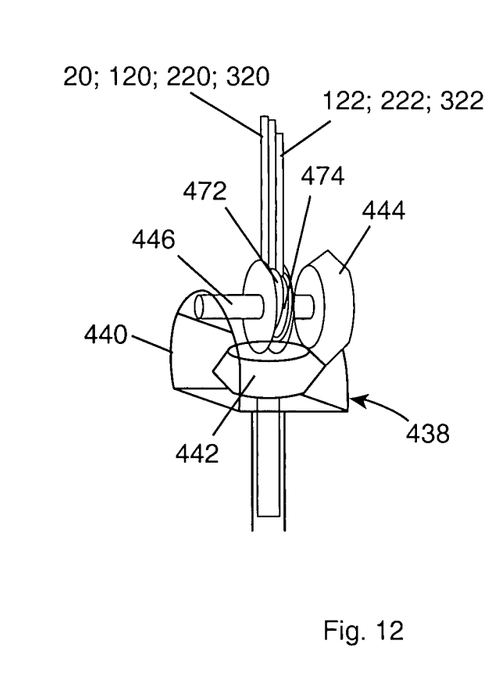
FIG. 12 illustrates part of a drive means for use with the heads of FIGS. 6, 7 and 11.

The first drive shaft 20, in use, is imparted a reciprocating motion by a further aspect (not shown) of the drive means, which may be any one of a number of known arrangements for generating reciprocating motion, and for example may be a variant of the arrangement shown in either FIG. 3 or 12, but adapted for use with the single drive shaft 20. The drive means further comprises translating means in the form of a crank shaped axle or crankshaft 26 located within the brush head 12, the ends of which are connected to the first and second hemispherical head sections 14, 16. The crankshaft 26 is driven by the reciprocating first drive shaft 20 in order to effect the simultaneous rotation of the head sections 14, 16 about a first axis, thereby effecting a first brushing motion of the head 12. The crankshaft 26 is preferably mounted on a support collar (not shown) or the like, providing support thereto.

The crankshaft 26 is also rotatable substantially about its longitudinal axis by means of the above mentioned further aspect (not shown) of the drive means, or by any other suitable means, in order to rotate the brush head 12 about a second axis, thereby effecting a second brushing motion of the head 12. The internal diameter of the shaft support sleeve 24 is reduced near its longitudinal centre and is progressively widened towards each end. The internal profile of the shaft support sleeve 24 provides support for the drive shaft 20 to enable it to rotate on its longitudinal axis.

In the embodiment illustrates the first and second axes are substantially perpendicular to one another. The axes also preferably extend through the centre of the spherical head 12. It will be appreciated that one or more electric motors may be used to provide the requisite drive to effect these first and second brushing motions.

The brush head 12 can be rotated clockwise or anti clockwise by switching the direction of current flow in the or each motor providing the drive. It will be appreciated from the above description that the brush head 12 may be continuously rotated in a single direction about the first and/or second axes, which provides a beneficial mode of operation. In addition, by stopping and starting and/or varying the voltage being supplied to the or each electric motor running the drive means, the brush head 12 can be made to move continuously in any direction, to reciprocate between two points or for any point on the surface of the head 12 to move through an arc continuously or to reciprocate through an arc.

Bristles 28 are fixed to the outer surface of each of the hemispherical head sections 14, 16 and placed at suitable positions on the hemispherical head sections 14, 16 to present a generally contiguous array of bristles 28 over the entire brush head 12. It will be appreciated that the bristles 28 could be arranged in any other suitable array, and could also be replaced with any other suitable functional equivalent.

The bristles 28 immediately proximate to the dividing channel 18 between the hemispherical head sections 14, 16 are inclined from the perpendicular to project over the channel 18. The bristles 28 on each hemispherical head section 14, 16, adjacent the channel 18, are therefore oriented to converge over the channel 18 in order to create a protective covering substantially surrounding the channel 18. This prevents the ingress of any foreign matter into the interior of the head 12. This also results in a substantially uniform concentration of bristles 28 across the surface of the brush head 12. In this way, a uniform concentration of bristles 28 is presented to the area of mouth being brushed irrespective of the orientation of the brush head 12.

When the hemispherical head sections 14, 16 rotate, the inclined bristles 28 flex as they pass the support sleeve 24 causing the bristles 28 to separate apart at that point. This enables the hemispherical head sections 14, 16 to rotate substantially unimpeded by the support sleeve 24.

Referring now to FIG. 3, there is illustrated a second embodiment of a toothbrush, generally indicated as 110, and in this second embodiment like components have been accorded like reference numerals, and unless otherwise stated, perform a like function.

Figure 4:
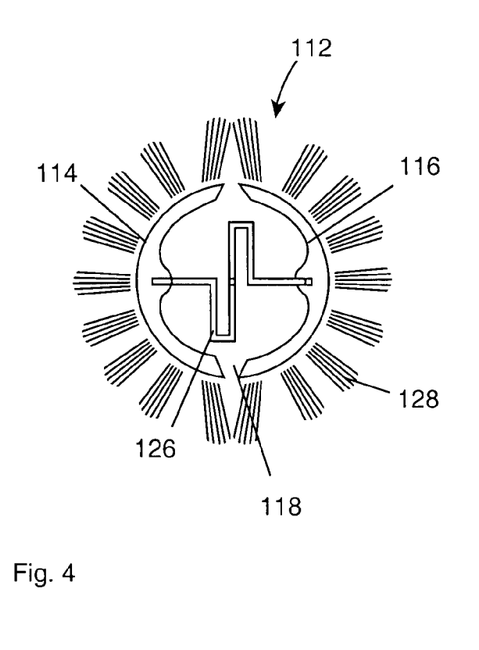
FIG. 4 is a cross sectional view of a head of the toothbrush illustrated in FIG. 3.

The toothbrush 110 again comprises a substantially spherical head 112 mounted adjacent the end of a sleeve 124 (which is in FIG. 3 represented by a schematically as a sectioned ring, in order to reveal the internal workings of the toothbrush 110). The head 112 comprises first and second hemispherical head sections 114, 116, with a channel 118 therebetween. An enlarged view of the head is shown in FIG. 4. As with the previous embodiment, the head 112 is provided with an array of bristles 128 thereon. Internally of the head 112, the first and second hemispherical head sections 114, 116 are joined by translating means in the form of a crank shaped axle or crankshaft 126, as will be described in greater detail hereinafter.

The toothbrush 110 further comprises drive means in the form of first and second motors 130, 132 which drive first and second motor shafts 134, 136 respectively. The first and second motor shafts 134, 136 are housed concentrically and are both connected to a transducer 138, which is adapted, as will be described, to convert the rotary motion of the motor shafts 134, 136 into both reciprocating and rotary motion. The transducer 138 comprises a frame 140 which is mounted to the second motor shaft 136, and is thus rotatable about a longitudinal axis of the motor shaft 136. The first motor shaft 134 passes through the frame 140, and is connected to, and therefore drives, a first bevel gear 142 which is mounted within the frame 140. The transducer 138 further comprises a second bevel gear 144 mounted orthogonally and in meshing engagement with the first bevel gear 142. Extending across the frame 140 from the second bevel gear 144 is a crankshaft 146. It will thus be appreciated that the first motor shaft 134 is capable of driving the second bevel gear 144 via the first bevel gear 142, and can thus drive the crankshaft 146.

Figure 5:
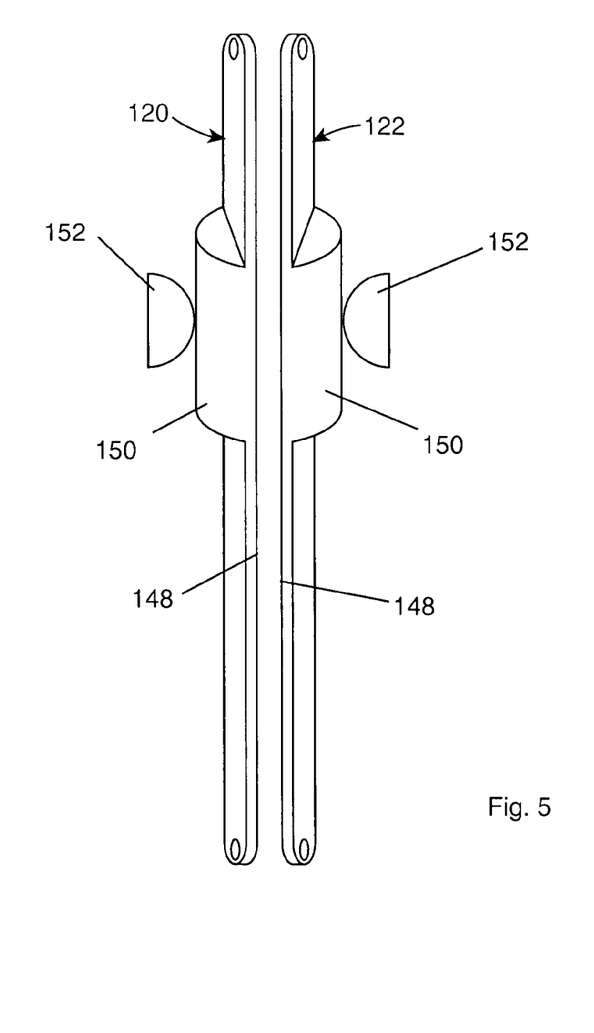
FIG. 5 is an enlarged view of a portion of the toothbrush illustrated in FIG. 3.

Extending from the crankshaft 146, in side by side alignment, and forming a further part of the drive means, is a first drive shaft 120 and a second drive shaft 122, which together extend through the sleeve 124 and into the head 112. One end of each of the drive shafts 120, 122 is connected to the crankshaft 146, while the other end of each of the drive shafts 120, 122 is connected to the crankshaft 126 located within the head 112. It will thus be appreciated that the first motor 130 may be used to drive the crankshaft 146, causing the drive shafts 120, 122 to reciprocate relative to one another, and therefore causing the first and second hemispherical head sections 114, 116 to rotate. Referring to FIG. 5, in order to provide stability to the drive shafts 120, 122 when reciprocating, each of the shafts 120, 122 is provided with a flat inner surface 148. The drive shafts 120, 122 are also flattened on the outside as they enter the head 112, in order to minimize the dimensions of the channel 118 that is required. Each of the shafts 120, 122 also include an outer rounded portion 150 which are held between a pair of slide and rotate bearings 152, as will be described hereinafter.

Thus the first motor 130 can be used to rotate the first and second hemispherical head section 114, 116 about a first axis as described above, in order to generate a first brushing motion. When it is desired to rotate the head 112 about a second axis, preferably perpendicular to the first axis, in order to generate a second independent brushing motion, the second motor 132 is employed. The second motor 132, when activated, rotates the second motor shaft 136, which is connected to the frame 140. This effects rotation of the entire frame 140, which rotates the drive shafts 120, 122 within the sleeve 124. The rotation is transmitted directly to the head 112, to effect the rotation thereof.

As the frame 140 rotates, the second bevel gear 144 will be drawn around the first bevel gear 142, which would act to rotate the first bevel gear 142, which is however mounted on the end of the first motor shaft 134. The first bevel gear 142 will experience resistance to rotation as a result of being connected to the second motor 132. For this reason, the rotation of the second bevel gear 144 about the first bevel gear 142 would result in rotation of the second bevel gear 144. This in turn would have the consequence of reciprocating the drive shafts 120, 122, and so effecting a combination of the first and second brushing motions at the same instance. While such a mode of operation is envisaged in the present invention, it is less preferred than having the first and second brushing motions independent of one another. Thus in order to allow rotation of the frame 140 without this result, it is preferable that a clutch (not shown) is provided between the first bevel gear 142 and the second motor shaft 136, in order to selectively break the drive train when rotation by the first motor 130 only is required. However, the two motors 130, 132 may be driven at the same time, effecting rotation of the head 112 about both axes simultaneously. When such a situation arises, the clutch need not be employed to break the drive train.

Turning to FIGS. 6-10, there is illustrated a third embodiment of a toothbrush, which is generally indicated as 210, and in this third embodiment like components have been accorded like reference numerals, and unless otherwise stated, perform a like function.

Figure 6:
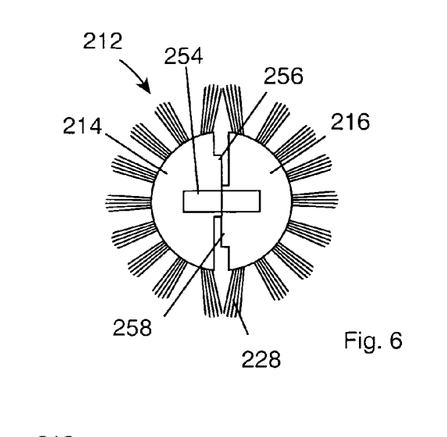
FIG. 6 is a cross sectional side view of a head of a toothbrush according to a third embodiment of the invention.
Figure 7:
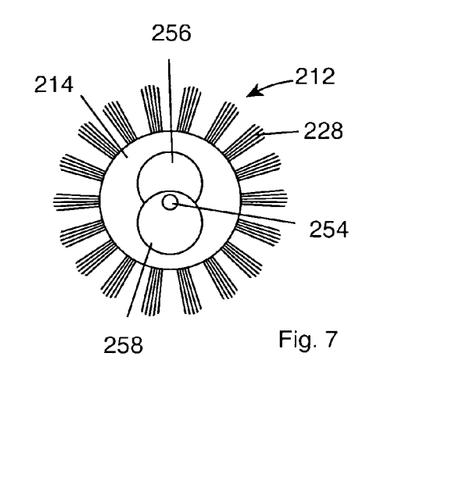
FIG. 7 is a cross sectional front view of the head of FIG. 6.

The toothbrush 210 comprises a substantially spherical head 212 having first and second hemispherical head sections 214, 216 mounted on a central axle 254, as illustrated in FIGS. 6 and 7. Translating means in the form of a circular cam protrusion 256 is provided on the first head section 214 and a similar cam protrusion 258 on the second head section 216. These protrusions 256, 258 are positioned eccentrically with respect to the axle 254.

Figure 8:
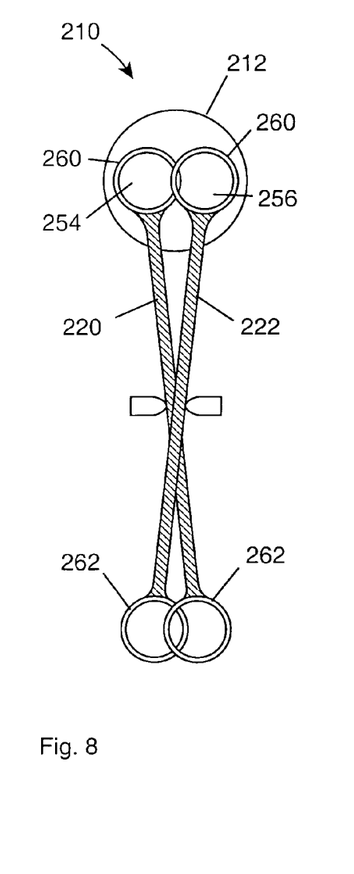
FIG. 8 is a cross sectional view of portion of a toothbrush according to the third embodiment, showing the head of FIG. 6.
Figure 9:
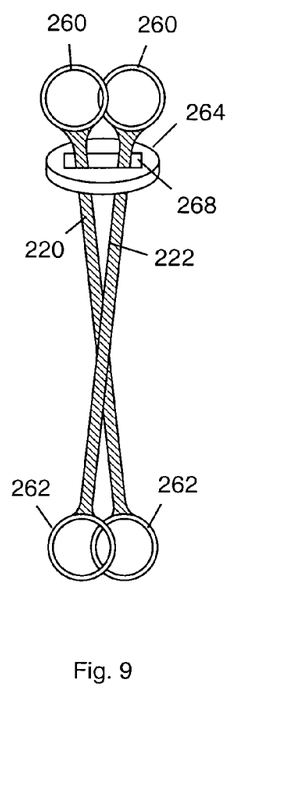
FIG. 9 is the view of FIG. 8 without the head of the toothbrush.
Figure 10:
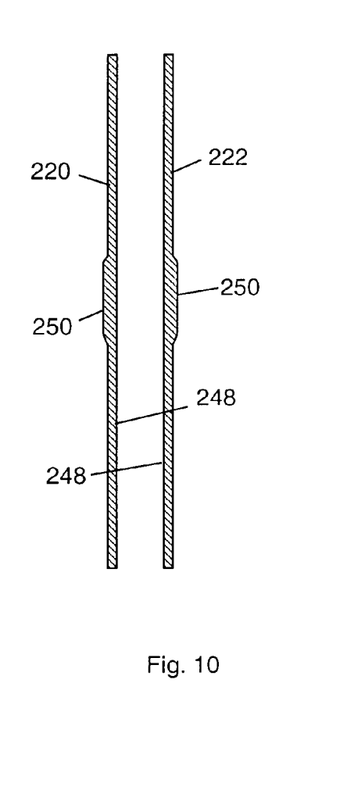
FIG. 10 is a side view of the toothbrush of FIGS. 8 and 9.

Referring to FIGS. 8-10, the toothbrush 210 further comprises a first drive shaft 220 and a second drive shaft 222, which operate in similar fashion to the drive shafts of the second embodiment described above. Each is provided with a ring like follower or coupling 260, which is seated about the respective cam protrusion 256, 258. At the opposed end of each drive shaft 220, 222, is provided an identical coupling 262, which is again ring like in shape, and is fitted, as will be described with respect to FIG. 12, to a further portion of the drive means, for effecting rotation of the head 212. Each of the drive shafts 220, 222 have a flat inner surface 248 and a curved portion 250, again as described with reference to the second embodiment. A guide 264 is preferably provided, having an elongate slot 268 through which the drive shafts 220, 222 pass. The slot 268 is shaped to allow the drive shafts 220, 222 to move in scissors like fashion relative to one another while preventing deflection of same in a direction normal to this movement, and with reference to FIGS. 8 and 9, in a direction into or out of the page. The guide 264 is circular in shape and is preferably rotatably mounted within an annular channel (not shown) at or adjacent the top of the tube (not shown) in which the drive shafts 220, 222 are housed. The guide 264 is therefore free to rotate when the drive shafts 220, 222 rotate to effect rotation of the brush head 212.

Figure 11:
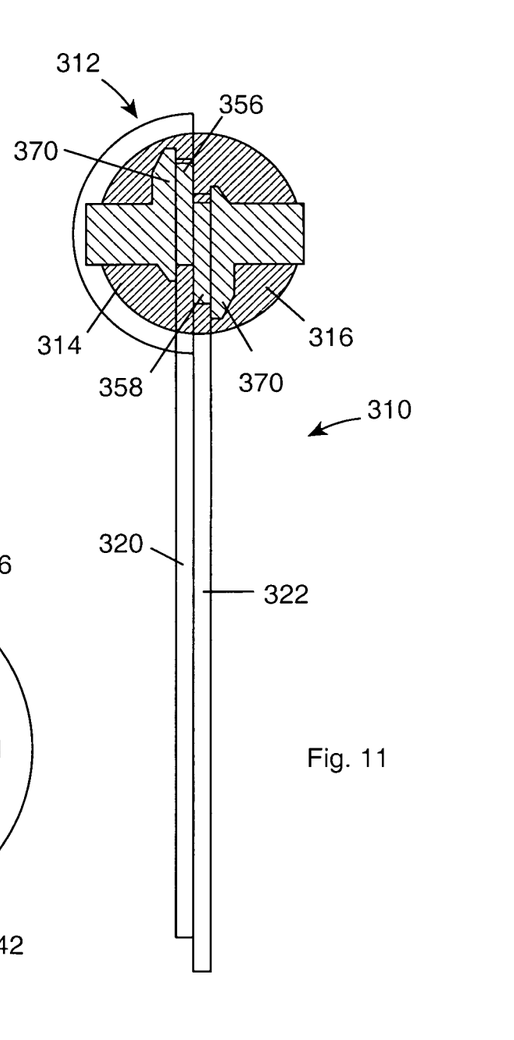
FIG. 11 is a cross sectional front view of a toothbrush head according to a fourth embodiment of the invention, which is similar to the head of FIGS. 6 and 7.

Referring now to FIG. 11 there is illustrated a toothbrush according to a fourth embodiment of the invention, generally indicated as 310, and in this fourth embodiment like components have been accorded like reference numerals, and unless otherwise stated perform a like function. The brush 310 comprises a brush head 312 which is very similar in configuration and operation to the head 210. The head comprises first and second head sections 314, 316, respectively having first and second cam protrusion 356, 358 internally thereof, and onto which first and second drive shafts 320, 322 are mounted as hereinbefore described with respect to the third embodiment. However, the head 310 is provided with a shoulder 370 on the exterior side of the first and second cam protrusion 356, 358, which prevent the ends of the drive shafts 320, 322 from being inadvertently disengaged from the cam protrusions 356, 358.

Referring now to FIG. 12, there is illustrated a transducer 438 which is adapted to convert the drive from a pair of motors (not shown) into first and second brushing motions of the brush head (not shown). This transducer 438 could be used with the toothbrush of the first second and third embodiments of the invention, although some basic modifications may be required, but which would be within the capabilities of a person skilled in the art. The transducer 438 comprises a frame 440 carrying a first bevel gear 442 and a second bevel gear 444, the second bevel gear 444 driving a crankshaft 446. Mounted on the crankshaft 446 are a pair of cams 472, 474 off-set relative to one another, to which in use the drive shaft(s) 20; 120, 122; 220, 222; 320, 322 of the toothbrush are connected. In this way, if the crankshaft 446 is driven by the second bevel gear 444, the pair of drive shafts will be forced to reciprocate relative to one another, thereby driving the two hemispherical head sections of the brush as hereinbefore described in order to effect the first brushing motion. However, if the frame 440 is driven about its longitudinal axis, the pair of drive shafts will rotate together in unison, in order to effect the simultaneous rotation of the two head sections about a longitudinal axis of the toothbrush in order to effect the second brushing motion.

Figure 13:
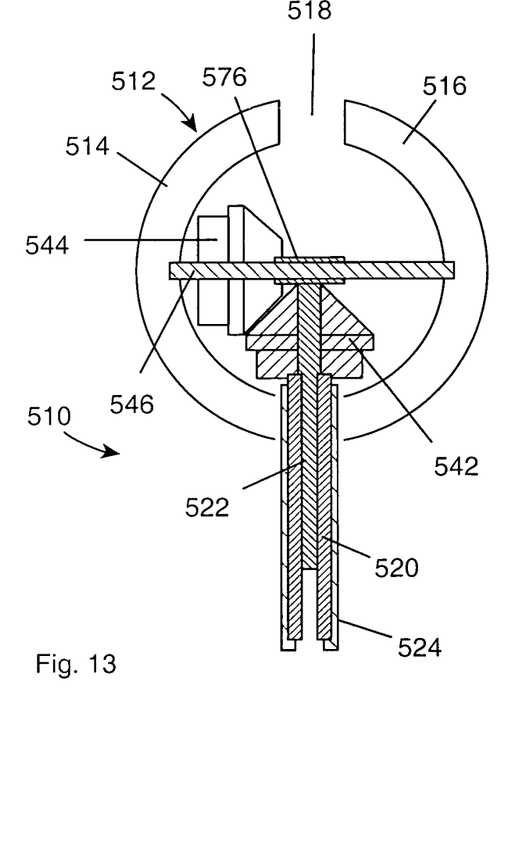
FIG. 13 illustrates a cross sectional front view of a toothbrush head according to a fifth embodiment of the invention.

Referring now to FIG. 13 there is illustrated part of a toothbrush according to a fourth embodiment of the present invention, generally indicated as 510. In this fourth embodiment like components have been accorded like reference numerals, and unless otherwise stated perform a like function. The toothbrush 510 again comprises a brush head 512, which is comprised of first and second hemispherical sections 514, 516 located at the end of a support sleeve 524 which may form part of an exterior handle or body of the toothbrush 510. The brush head 510, as with previous embodiments, is preferably covered with an array of bristles (not shown) or any other suitable functional equivalent. The first and second head sections 514, 516 are slightly separated from one another, thereby defining a channel 518 which provides access to first and second drive shafts 520, 522 to the interior of the head. In this fourth embodiment, the first and second drive shafts 520, 522 are located concentrically within one another, and in addition concentrically within the support sleeve 524. The first and second drive shafts 520, 522 form part of drive means of the toothbrush 510. The drive means further comprises translating means in the form of first bevel gear 542 fixed to the first drive shaft 520 and a meshing second bevel gear 544, which is mounted on an axle 546. Either end of the axle is then fixed to the respective hemispherical head section 514, 516. The axle 546 is retained within a support 576 which is secured at the free end of the second drive shaft 522, which passes upwardly through the first drive shaft 520 and through the centre of the first bevel gear 542.

It will thus be appreciated that by driving the first drive shaft 520 independently of the second drive shaft 522, the hemispherical head sections 514, 516 will be continuously rotated about a first axis corresponding to a longitudinal axis of the axle 546, thereby effecting a first brushing motion of the head 512. If the first drive shaft 520 is then stopped and the second drive shaft 522 driven independently thereof, the entire axle 546, by virtue of being mounted within the support 576, will be rotated about a second axis corresponding to a longitudinal axis of the first and second drive shafts 520, 522. This rotation of the axle 546 will therefore effect a simultaneous rotation of the pair of hemispherical head sections 514, 516, thereby effecting a second brushing motion. The first and second axes, about which the head 512 rotates, are substantially perpendicular to one another.

Although not illustrated, it will be appreciated that the first and second drive shafts 520, 522 could be driven by any suitable means, for example, one or two electric motors (not shown) or the like. It will also be appreciated that other than driving one and/or the other first and second drive shaft 520, 522 continuously in a single direction, either drive shaft could be oscillated in order to impart a similar oscillating motion to the brush head 512 as part of either the first or second brushing motion.

Figure 14:
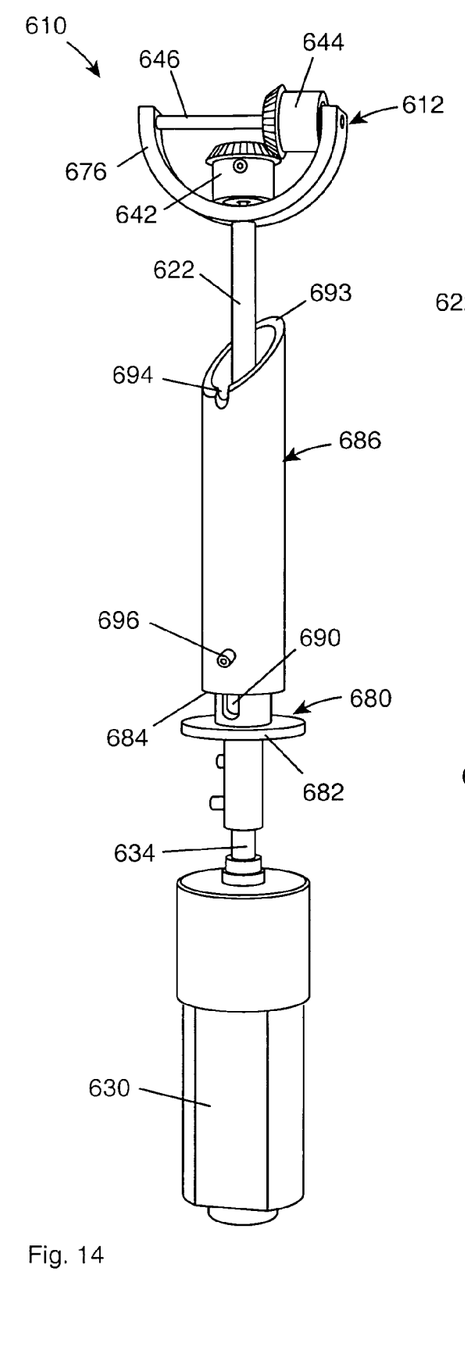
FIG. 14 illustrates a perspective view of the internal workings of a toothbrush according to a sixth embodiment of the invention, with a clutch thereof in a disengaged position.
Figure 15:
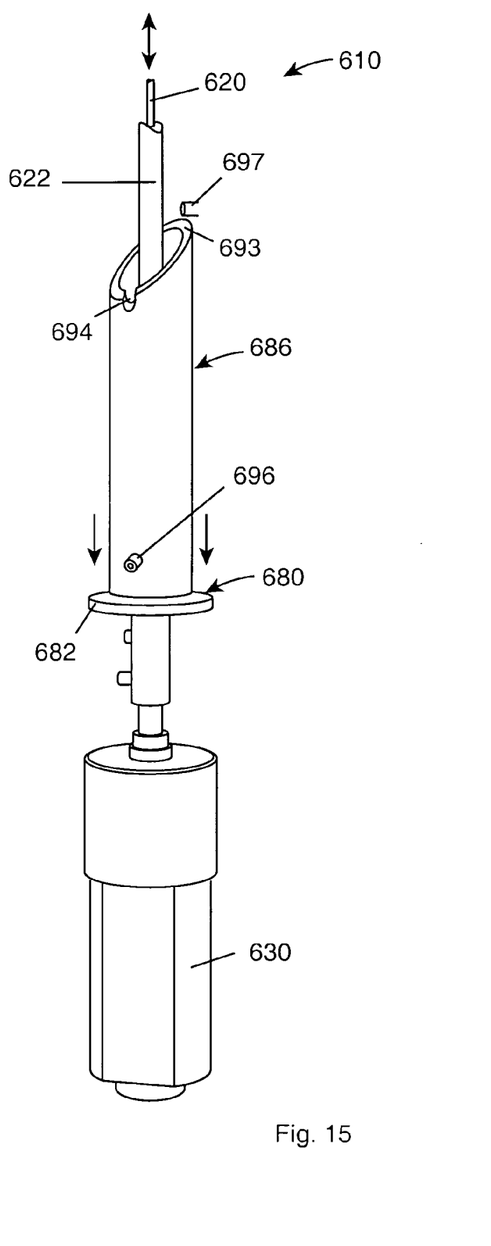
FIG. 15 illustrates the toothbrush of FIG. 14 with the clutch in an engaged position.
Figure 16:
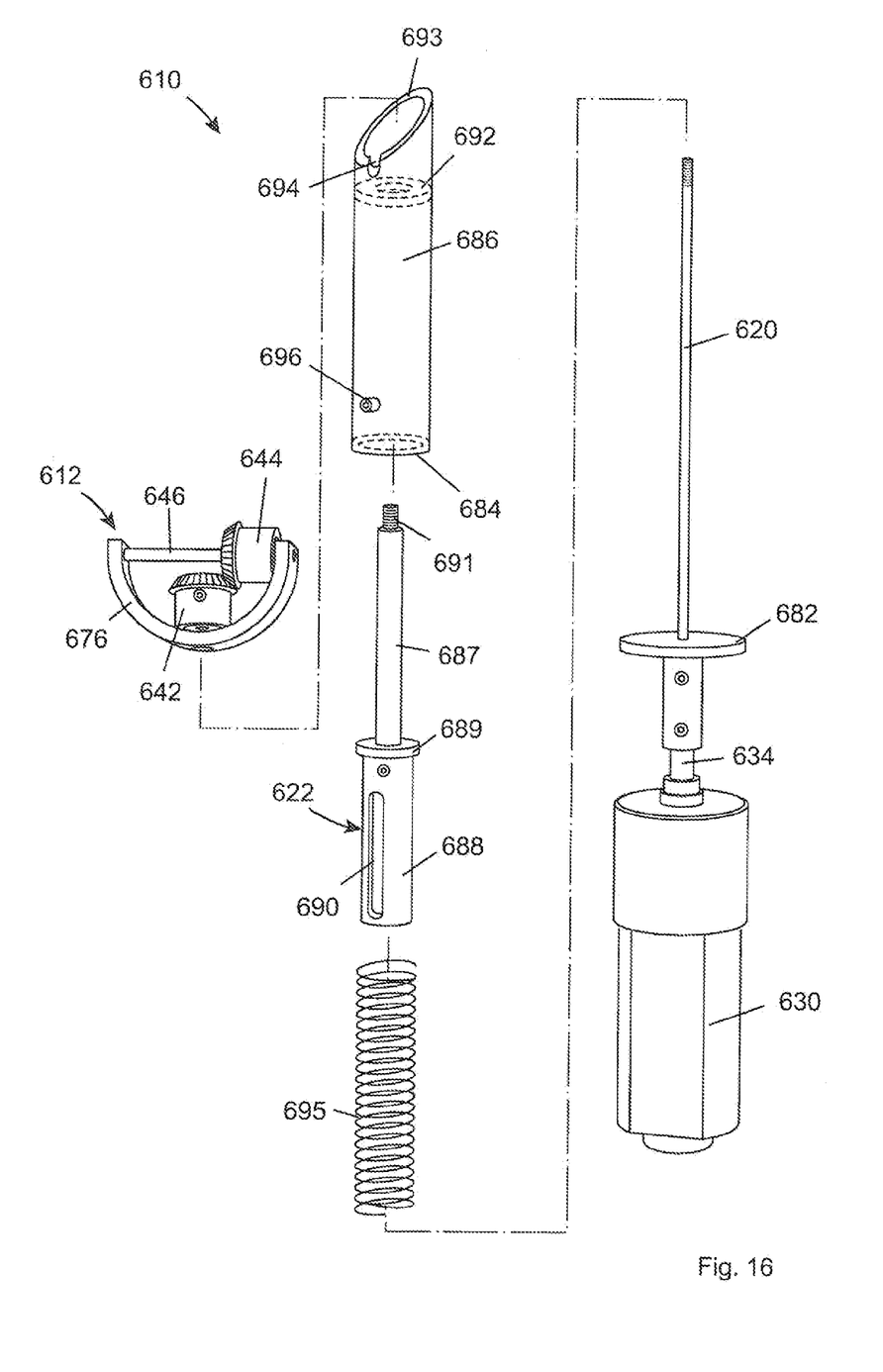
FIG. 16 illustrates an exploded view of the toothbrush of FIGS. 14 and 15.

Turning now to FIGS. 14 to 16 there is illustrated a fifth embodiment of a toothbrush according to the present invention, generally indicated as 610. In this fifth embodiment like components have been accorded like reference numerals, and unless otherwise stated perform a like function.

The toothbrush 610 again comprises a substantially spherical head 612 although only the interior workings thereof are illustrated in FIGS. 14 and 16, and is entirely omitted from FIG. 15. FIGS. 14 to 16 show the basic internal workings of the toothbrush 610, and it will be appreciated that in use this would be surrounded by a suitable casing, preferably defining a handle portion, a section in which to locate a battery or the like, and any circuitry associated with the operation of the toothbrush 610.

The toothbrush 610 comprises a first drive shaft 620 and a second drive shaft 622 located concentrically thereabout. The toothbrush 610 does however only comprise a single motor 630 which, as will be described hereinafter, is operable to drive both drive shafts 620, 622. In order to achieve this the toothbrush 610 comprises a clutch 680 which is mounted to a shaft 634 of the first motor 630 and is therefore rotatable therewith. The clutch 680 may be of any suitable form, for example a friction based clutch, a magnetic clutch, or any other functional equivalent. In the present embodiment, the clutch 680 is a friction based clutch and comprises a first clutch plate 682 which is fixed to and therefore rotates with the motor shaft 634 and the first drive shaft 620. The clutch 680 further comprises a second clutch plate 684 which is formed at the free end of a sleeve 686 which is displaced longitudinally over the second drive shaft 622 in order to engage and disengage the first and second clutch plate 682, 684. In FIG. 14 the clutch 680 is shown in the disengaged state, while in FIG. 15 the clutch 680 is shown in the engaged state. In the disengaged state the motor 630 will drive only the first drive shaft 620, while when in the engaged state the motor 630 will, via the clutch 680, synchronously drive both the first and second drive shafts 620, 622, as will be described in greater detail hereinafter.

Referring in particular to FIG. 16, it can be seen that the first drive shaft 620 is fixed to the first clutch plate 682 and therefore rotates therewith. The second drive shaft 622 is hollow and when the toothbrush 610 is assembled is located around the first drive shaft 620. The second drive shaft 622 comprises a first section 687 and a second section 688 which are divided by a shoulder 689. The second section 688 is provided with an elongate slot 690 therein, while the first section 687 has a threaded end 691.

Referring to the clutch sleeve 686, an annular shoulder 692 is provided internally thereof adjacent a tapered end 693, in which there is provided a notch 694 at the inner most point of the tapered end 693. The annular shoulder 692 is dimensioned to permit the passage of the first section 687 of the second drive shaft 622 therethrough while preventing passage of the shoulder 689. The toothbrush 610 further comprises a spring 695 which is dimensioned to be located over the second section 688 of the second drive shaft 622, but is arrested by the shoulder 689, thereby allowing the spring to be compressed against the shoulder 689. During assembly, the second drive shaft 622 is slid into the sleeve 686, such that the first section 687 projects through the annular shoulder 692 and out of the tapered end 693. The spring 695 is then advanced into the sleeve 686 and around the second section 688 to abut against the shoulder 689. The spring is then compressed until the end thereof opposite the shoulder 689 passes a grub screw 696 located in the sleeve 686. The grub screw 696 can then be advanced through the side wall of the sleeve 686 and into the elongated slot 690. The grub screw 696 will therefore prevent extension of the spring 695, thereby maintaining tension therein. This entire assembly is then positioned over the second drive shaft 622 as illustrated in FIG. 15, and the head 612 is then mounted onto the drive shafts 620, 622 as illustrated in FIG. 14. The interior of the head 612 comprises a first bevel gear 642 which is threaded onto the free end of the first drive shaft 620, and a second bevel gear 644 which is mounted on an axle 646 which is itself contained on a support 676. The support 676 is threaded onto the threaded end 691 of the second drive shaft 622. The second drive shaft 622 is therefore fixed longitudinally between the first dutch plate 682 and the support 676.

Turning then to the operation of the toothbrush 610, and referring initially to FIG. 15, a first brushing motion may be affected with the clutch 680 engaged. In this mode of operation, the motor 630 is driving the first drive shaft 620, which therefore drives the clutch 680, resulting in the synchronised rotation of the outer drive shaft 622. This is as a result of the location of the grub screw 696 within the elongated slot 690, which fixes the sleeve 686 to the second drive shaft 622 in the rotational sense, but allows longitudinal displacement of the sleeve 686 relative to the second drive shaft 622, as the grub screw 696 can slide up and down within the elongated slot 690, although against the action of the compressed spring 695. It is the compressed spring 695 that forces the sleeve 686, and in particular the second clutch plate 684, against the first clutch plate 682 in order to maintain the clutch 680 in the engaged position. With the two drive shafts 620, 622 rotating in unison, both the support 676 carrying the axle 646, and the first bevel gear 642 mounted on the first drive shaft 620, will rotate together. This results in the brush head 612 rotating about an axis corresponding to a longitudinal axis of the first and second drive shafts 620, 622, in order to effect the first brushing motion. By rotating the first bevel gear 642 with the support 676, and at the same speed, rotation of the second bevel gear 644 on the axle 646 is prevented. If the first bevel gear 642 were stationary then rotation of the support 676 would draw the second bevel gear 644 around the stationary first bevel 642, thus causing the second bevel gear 644 to rotate on the axle 646. This allows the first and second brushing motions to be achieved independently of one another.

Turning then to FIG. 14, in order to disengage the clutch 680 the sleeve 686 is drawn away from the clutch plate 680, against the action of the spring 695. Suitable retaining means (not shown) may be provided in order to retain the sleeve 686 out of engagement with the clutch plate 682. These retaining means may be of any suitable form, for example one or more detent balls (not shown) acting on the exterior of the sleeve 686, or any other suitable functional equivalent. The retaining means are preferably disengagable manually from an exterior of the toothbrush 610 although it will be appreciated that an electronic means of release may be employed. Similarly, a switch/lever or the like (not shown) operable to slide the sleeve 686 between the engaged and disengaged positions, is preferably accessible from the exterior of the toothbrush 610, although again an electronic equivalent may be employed.

Once the clutch 680 has been disengaged, the motor 630 will drive only the first drive shaft 620 and therefore will drive the first bevel gear 642 while the support 676 remains stationary. This will thus drive the second bevel gear 644 which will then rotate the two hemispherical head sections (not shown), which in use are mounted on either end of the axle 646, about an axis that corresponds with a longitudinal axis of the axle 646. This simultaneous rotation of the hemispherical head sections results in the second brushing motion, whose direction is substantially perpendicular to the direction of the first brushing motion.

It will be appreciated that while the first and second brushing motions are substantially perpendicular to one another, and will always remain so, it will often be desirable to correctly orient these brushing motions with respect to the user's teeth. For the first brushing motion, the user will always know the directional rotation of the brush head 612 as it is about an axis which corresponds to a longitudinal axis of the first and second drive shafts 620, 622, which will be located internally of a handle or shaft portion of the toothbrush which can then be used as a point of reference. However, the angular orientation of the axle 646 on which the hemispherical head sections rotate during the second brushing motion will not be apparent to the user when initiating the second brushing motion, as it is located internally of the brush head 612. It is, for example, desirable to have the axle 646 substantially parallel to the surface of the user's teeth when utilising the second brushing motion, in particular when brushing the front or rear surface of the front teeth. Thus it is desirable to ensure that the axle 646 is in a pre-determined location once the clutch 680 is disengaged such as to initiate the second brushing motion. To this end the toothbrush 610 is provided with positioning means which are partially defined by the tapered end 693 and the notch 694. The positioning means further comprises a pin 697 which in use is fixed to the inner surface of the exterior body or casing (not shown) of the toothbrush 610 within which the first and second drive shafts 620, 622 will be housed during use. The pin 697 is located slightly upstream of the tapered end 693 of the sleeve 686 when the clutch 680 is in the engaged position. It will then be appreciated that as the sleeve 686 is drawn away from the clutch plate 682 into the disengaged position, the tapered end 693 will contact the pin 697, the two then acting like a cam and follower. Thus the sleeve 686 will be forced to rotate around the pin 697 thus resulting in the corresponding rotation of the second drive shaft 622, and thus the support 676 and the axle 646. The sleeve 686 will eventually rotate until the notch 694 comes into register with and then receives the pin 697. This corresponds to the fully disengaged position of the clutch 680, which is then held in this position by the above-mentioned retaining means (not shown). As the pin 697 is fixed relative to the exterior of the toothbrush 610, once the clutch 680 has been fully disengaged, regardless of the initial position of the second drive shaft 622 when the clutch 680 is first moved from the engaged towards the disengaged position, the final position of the sleeve 686, and thus by association the axle 646, will always be the same. This then provides the user with a point of reference which indicates the direction in which the second brushing motion occurs, thereby allowing the direction of the second brushing motion to be oriented as desired relative to the user's teeth. A simple indicia or the like may be provided on the exterior of the toothbrush body in order to indicate this point of reference, or it may be oriented relative to a particular portion of the toothbrush, for example a handle or switch (not shown) thereof.

It will be appreciated that, if necessary, a similar or functionally equivalent positioning means may be employed with any of the other embodiments of the invention as described herein.

Figure 17:
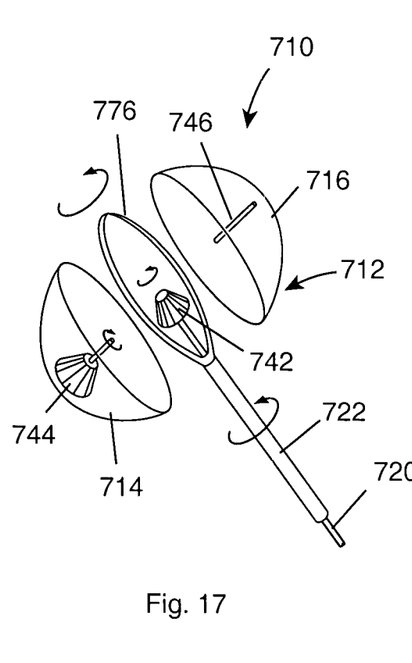
FIG. 17 illustrates an exploded view of a head of a toothbrush according to a seventh embodiment of the invention.
Figure 18:
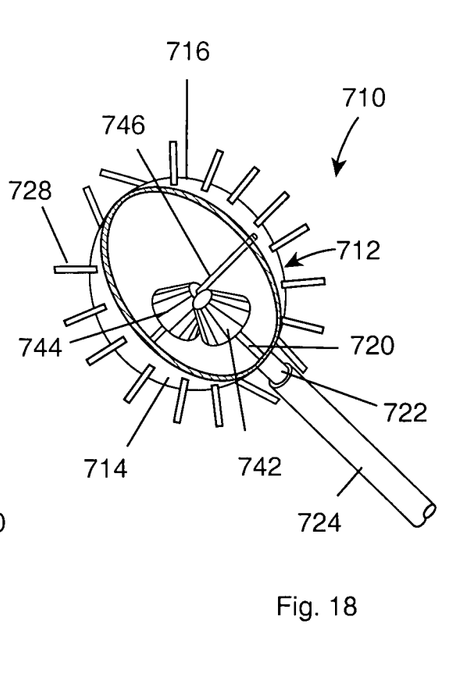
FIG. 18 illustrates a partially cut away view of the head of FIG. 17.

Referring now to FIGS. 17 and 18 there is illustrated a sixth embodiment of a toothbrush according to the present invention, generally indicated as 710. In this sixth embodiment like components have been recorded like reference numerals, and unless otherwise stated will perform a like function.

Only a portion of the toothbrush 710 is illustrated, showing a head 712 and drive means in the form of drive shafts 720, 722 housed within a support sleeve 724, which is not however illustrated in FIG. 17. The brush head 712 comprises first and second hemispherical head sections 714, 716 which are provided with an array of bristles 728 thereon. The first drive shaft 720 is located concentrically within the second drive shaft 722, which is itself located concentrically within the support sleeve 724. Extending from the free end of the second drive shaft 722 is an annular support 776 which corresponds in shape and dimension to the edges of the hemispherical head sections 714, 716 and against which in use the edges of the hemispherical head sections 714, 716 are engaged and rotatable on.

Mounted to the free end of the second drive shaft 722 is a first bevel gear 742, while a meshing second bevel gear 744 is mounted on an axle 746 on either free end of which is mounted one of the hemispherical head sections 714, 716. In this way independent rotation of the second drive shaft 722 will effect rotation of the hemispherical head sections 714, 716 about a first axis corresponding to a longitudinal axis of the axle 746, with the annular support 776 acting as a bearing or bushing, in order to effect a first brushing motion. Similarly, independent rotation of the second drive shaft 722 will effect rotation of the support 776 thus simultaneously rotating the hemispherical head sections 714, 716 about a second axis corresponding to a longitudinal axis of the first and second drive shafts 720, 722, in order to effect the second brushing motion. Unlike in the previous embodiments, the annular support 776 closes the channel between the hemispherical head sections 714, 716, thereby preventing the ingress of any foreign material to the interior of the head 712.

The operation of the toothbrush 10, 110, 210, 310, 510, 610, 710 may be controlled by any suitable means. It can be fully manually controlled by having a four or eight point toggle switch. The toothbrush 10, 110, 210, 310, 510, 610, 710 can also be semi automatically controlled by having combined automatic and manual controls.

Manual four way switching provides convenient brushing directly off the gum in all locations in the mouth. This may also provide convenient forward only tongue brushing.

The following is a table of a sample switch actions model to rotate the brush head in a particular plane and direction:

| Switch | Direction | Plane |
|---|---|---|
| North | clockwise | vertical |
| South | anti clockwise | vertical |
| East | clockwise | horizontal |
| West | anti clockwise | horizontal |

Manual eight way switching provides the same control as manual four way switching and in addition can enable the modified bass method brushing action to be replicated. The following table shows a sample switch action model to rotate the brush head simultaneously in particular planes and directions:

| Switch | Brush rotation action |
|---|---|
| Northwest | Clockwise in vertical plane and anticlockwise in horizontal plane |
| Northeast | Clockwise in vertical plane and clockwise in horizontal plane |
| Southwest | Anti clockwise in vertical plane and clockwise in horizontal plane |
| Southeast | Anti clockwise in vertical plane and clockwise in horizontal plane |

Gravity switches can be used as the above mentioned positioning means to ensure the direction of rotation in the vertical plane is selected automatically. This facilitates brushing in the rearward face of the upper and lower front teeth as the brush head automatically rotates in the appropriate direction when the device is oriented in suitable direction for cleaning the rearward face of the upper or lower front teeth.

Manual or automatic switching can be selected by the user. For example, a switch can be used to select automatic mode to disable a manual toggle switch. The user can then only manually control clockwise or anti clockwise motion of the brush head in the horizontal plane. This simplifies the use of the toothbrush 10, 110, 210, 310, 510, 610, 710 for the operator.

The brushing motion of the toothbrush 10, 110, 210, 310, 510, 610, 710 can also be fully automatically controllable. For example, brushing motion sequences can be stored in a memory chip in the toothbrush 10, 110, 210, 310, 510, 610, 710 and can be automatically selected or manually selected by the user before brushing commences. For example, there can be predetermined brushing sequences for brushing a child's teeth, gums and tongue or for brushing an adult's teeth gums and tongue.

It will be appreciated that the driving mechanism can be any suitable mechanical layout which affords the requisite properties and not necessarily as herein described.

It will be appreciated the toothbrush may be used for cleaning human, animals or other creatures teeth, gums, tongue or any other part of the mouth. It will also be appreciated the toothbrush may be employed for cleaning any other surface having the requisite properties.

The vertical plane is the plane through which the longitudinal axis of the brush axis passes and horizontal planes lies perpendicular to this vertical plane. It will be appreciated that the vertical and horizontal planes can be any other planes which are substantially perpendicular to one another in which the toothbrush head may rotate.

It will also be appreciated that a drive to the head may be provided by any suitable means, for example by using some form of hydraulic arrangement. In addition, the sleeve connecting the body of the toothbrush to the head may be provided with a flexible or deformable joint therein, in order to allow the head to be bent at an angle to the body of the toothbrush.

The invention claimed is:

1. A toothbrush comprising a substantially spherical brush head comprising two substantially hemispherical sections separated from one another by a channel; and drive means extending through the channel and adapted to impart at least first and second independent brushing motions to the head.

2. A toothbrush according to claim 1 in which the head is rotatable about a first axis when undergoing the first brushing motion and independently about a second axis when undergoing the second brushing motion.

3. A toothbrush according to claim 2 in which the first and second axes are substantially perpendicular.

4. A toothbrush according to claim 2 in which the first and second axes pass through the centre of the head.

5. A toothbrush according to claim 2 in which the head is continuously rotatable in a given direction about the first and/or second axis.

6. A toothbrush according to claim 1 in which the head comprises an array of bristles extending outwardly therefrom.

7. A toothbrush according to claim 6, in which the bristles on the first and second hemispherical sections, at or adjacent the interface between the sections, are oriented to converge in order to create a protective covering substantially surrounding the interface.

8. A toothbrush according to claim 1 in which the drive means comprises at least one drive shaft arranged to impart one or both brushing motions to the head.

9. A toothbrush according to claim 8 in which the at least one drive shaft is arranged to reciprocate in order to impart the first brushing motion to the head, and to rotate substantially about a longitudinal axis of the drive shaft in order to impart the second brushing motion to the head.

10. A toothbrush according to claim 9 in which the drive means comprises means for translating the reciprocating motion of the at least one drive shaft into rotary motion of the head about a first axis.

11. A toothbrush according to claim 10 in which the translating means comprises a crankshaft.

12. A toothbrush according to claim 10 in which the translating means comprises at least one cam connected to the head and a corresponding follower connected to the drive shaft.

13. A toothbrush according to claim 12 in which the follower comprises a bushing surrounding the cam.

14. A toothbrush according to claim 8 in which the drive means comprises first and second drive shafts, the first shaft being arranged to impart the first brushing motion to the head and the second shaft being arranged to impart the second brushing motion to the head.

15. A toothbrush according to claim 14 in which the first and second drive shafts are concentric.

16. A toothbrush according to claim 14 in which the drive means comprises at least one motor arranged to drive the first and second shafts.

17. A toothbrush according to claim 14 in which the drive means comprises a clutch displaceable between an engaged and a disengaged state, in the engaged state enabling synchronous rotation of the first and second shafts, and in the disengaged state enabling independent rotation of the first shaft.

18. A toothbrush according to claim 17 comprising means for immobilising the second shaft, in a predetermined orientation, when the clutch is in the disengaged state.

19. A toothbrush according to claim 14 in which the drive means comprises a pair of bevel gears located within the head, a first gear fixed to the first shaft and a second gear meshing with the first gear and mounted on an axle to which the pair of hemispherical head sections are mounted.

20. A toothbrush according to claim 19 in which the second shaft is connected to a support which carries the axle.

21. A toothbrush according to claim 19 in which the second shaft is connected to a support on which the head is retained.

22. A toothbrush comprising a substantially spherical brush head; and drive means adapted to impart at least first and second independent brushing motions to the head; wherein the first independent brushing motion comprises continuous rotation of the brush head about a first axis, and the second independent brushing motion comprises continuous rotation of the brush head about a second axis substantially perpendicular to the first axis.

23. A toothbrush according to claim 22 in which the orientation of the second axis relative to a point of reference on the toothbrush may be manually or automatically selected.

* * * * *